US00PP19083P3

(12) United States Plant Patent
Olesen

(10) Patent No.: US PP19,083 P3
(45) Date of Patent: Aug. 12, 2008

(54) MINIATURE ROSE PLANT NAMED 'POULPAR040'

(50) Latin Name: ***Rosa* hybrid**
Varietal Denomination: Poulpar040

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 297 days.

(21) Appl. No.: 11/360,400

(22) Filed: Feb. 22, 2006

(65) Prior Publication Data

US 2007/0199112 P1 Aug. 23, 2007

(51) Int. Cl.
*A01H 5/00* (2006.01)

(52) U.S. Cl. ..... Plt./121

(58) Field of Classification Search ..... Plt./121
See application file for complete search history.

*Primary Examiner*—Annette H Para

(57) ABSTRACT

A new miniature rose plant that has abundant, pink flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar040'.

SUMMARY OF THE INVENTION

The present invention constitutes a new and distinct variety of miniature rose plant which originated from a controlled crossing between the female seed parent, an 'Poulra002', U.S. Plant Pat. No. 13,275, and the male pollen parent an unnamed seedling.

The two parents were crossed during the summer of 2002 and the resulting seeds were planted in a controlled environment in Fredensborg, Denmark. The new variety, named 'Poulpar040', originated as a single seedling from the stated cross.

The new variety may be distinguished from its female seed parent by the following combination of characteristics:

1. The seed parent has a flowers which are generally Red 43 C in color. 'Poulpar040' has flowers which are generally Red group 55A to 55B.
2. The new variety has a unique flower form which distinguishes it from the seed parent variety.

The new variety may be distinguished from its male pollen parent primarily by flower color. 'Poulpar040' flowers are generally medium pink in color, while the pollen parent flowers are lighter pink.

The objective of the hybridization of this rose variety for commercial culture was to create a new and distinct variety with unique qualities, such as:

1. Uniform and abundant medium pink flowers;
2. Vigorous and compact growth;
3. Year-round flowering under glasshouse conditions;
4. Suitability for production from softwood cuttings in pots; and
5. Durable flowers and foliage which make a variety suitable for distribution in the floral industry.

This combination of qualities is not present in previously available commercial cultivars of this type, known to the inventor, and distinguish 'Poulpar040' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar040' was selected by the inventor as a single plant from the progeny of the hybridization in 2003.

Asexual reproduction of 'Poulpar040' by cuttings and traditional budding was first done by Mogens N. Olesen in the nursery in Fredensborg, Denmark in April 2003. This initial and other subsequent propagations conducted in controlled environments have demonstrated that the characteristics of 'Poulpar040' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar040'. Specifically illustrated in the drawing:

FIG. 1.1; Flower buds at various stages of opening;

FIG. 1.2; Cluster of open flowers and open flower viewed from above;

FIG. 1.3; Sepals, receptacle, pedicel, and reproductive flower parts;

FIG. 1.4; Bare stem;

FIG. 1.5; Flower petals, detached; and

FIG. 1.6; Leaves.

DETAILED DESCRIPTION OF THE VARIETY

The following is a description of 'Poulpar040', as observed in its growth in a glasshouse in Fredensborg, Denmark. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra024', U.S. Plant Pat. No. 15,017 are compared to 'Poulpar040' in Chart 1.

CHART 1

| Characteristic | 'Poulpar040' | 'Poulra024' |
|---|---|---|
| Color of petal upper surface | 62A to 58D | 58B |
| Petalage | 70 to 80 | 20 to 40 |

FLOWER AND FLOWER BUD

Blooming habit: Continuous.

Flower bud:

*Size.*—Upon opening, 20 mm in length from base of receptacle to end of bud. Bud diameter is 10 to 11 mm.

*Bud form.*—Urceolate.

*Bud color.*—As sepals unfold, petals are Red Group 52B to 55A.

*Sepals.*—Upper Surface: Color: Green Group 138A to 138B. Texture: Weak Pubescence. Lower Surface: Color: Yellow-Green Group 146A with occasional anthocyanic pigments colored Greyed-Red Group 181A at apex. Texture: Somewhat rough with many stipitate glands. Shape: Apex: Cirrhose. Base: Flat at union with receptacle. Margins: Margins have strong foliaceous appendages on three of the five sepals. Stipitate glands are abundant. Size: 30 mm long by 13 mm wide.

*Receptacle.*—Surface Texture: Smooth. Shape: Urn-shaped. Size: 7 mm (h)×8 mm (w). Color: Yellow-Green Group 144A to 144B.

*Pedicel.*—Surface: Somewhat rough with stipitate glands. Length: 20 to 25 mm. Diameter: 2 to 2.5 mm. Color: Yellow-Green Group 144B. Strength: Medium strength. Scent: Stipitate glands release a strong pine scent when touched.

*Borne.*—Flowers are borne in small clusters of 3 to 4 buds per flowering stem on average. Inflorescence type is a panicle.

Flower bloom:

*Fragrance.*—Light floral scent.

*Duration.*—As a pot plant, flowers last up to 28 days. Petals do not fall cleanly away from plant after flowers have fully matured.

*Size.*—Average flower diameter is 50 mm. Normal flower depth is 18 to 20.

*Form.*—Flowers resemble a star shaped rosette with many overlapping petals of various sizes.

*Shape of flower, side view.*—Upon opening: The upper portion is flat. The lower portion is flat. After opening: The upper portion is flattened convex. The lower is slightly concave.

Petalage: There are normally 70 to 80 petals under normal conditions, 10 of which are petaloids.

Color:

*Upon opening, petals.*—Outermost petals: Upper Surface: Red-Purple Group 62A to Red Group 58D. Lower Surface: Red-Purple Group 62D to 62B with an occasional streak bisecting of Red-Purple Group 65D. Occasionally, the outer guard petals have streaks of Green Group 142B and 142C. Innermost petals: Upper Surface: Red-Purple Group 62A to Red Group 58D. Lower Surface: Red-Purple Group 62A to 62B with an occasional streak bisecting the petal of Red-Purple Group 65D. Basal petal spots upon opening: Upper surface: Green-Yellow Group 1D. Lower surface: Green-Yellow Group 1D.

*After opening, petals.*—Outermost petals: Outermost petals: Upper Surface: Red-Purple Group 62A to Red Group 58D. Lower Surface: Red-Purple Group 62D to 62B with an occasional streak bisecting of Red-Purple Group 65D. Outer guard petals occasionally have streaks of Green Group 142B and 142C. Innermost petals: Upper Surface: Red-Purple Group 62A to Red Group 58D. Lower Surface: Red-Purple Group 62A to 62B with an occasional streak bisecting the petal of Red-Purple Group 65D. Basal petal spots upon opening: Upper surface: Green-Yellow Group 1D. Lower surface: Green-Yellow Group 1D.

General tonality: On open flower Red Group 55A to 55B. No change in tonality at the end of the $10^{th}$ day.

Petals:

*Petal reflex.*—Medium petal reflex at margins.

*Petal margin.*—Entire with weak undulations.

*Shape.*—Generally narrow elliptical. Base: Acute. Apex: Pointed or acute.

*Size.*—Petal size varies. Outer petals are normally 30 mm (l)×22 mm (w). Inner petals are typically 20 mm (l)×15 mm (w).

*Texture.*—Slightly rough.

*Thickness.*—Average.

Petaloids:

*Quantity.*—10 on average.

*Size.*—16 mm long×12 mm wide.

*Shape.*—Apex is pointed. Base is acute.

*Color.*—Upper Surface: Red-Purple Group 62A to Red Group 58D. Lower Surface: Red-Purple Group 62D to 62B with an occasional streak bisecting of Red-Purple Group 65D.

Reproductive organs:

*Pollen.*—None observed.

*Anthers.*—Size: 2 mm long. Color: Orange-White Group 159D. Quantity: 75 to 85.

*Filaments.*—Color: Orange-White Group 159D. Length: 5 mm.

*Pistils.*—Length: 2 to 3 mm long. Quantity: 45 to 50.

*Stigmas.*—Inferior in relative to the length of the filaments and the height of the anthers. Color: Greyed-Yellow Group 162D.

*Styles.*—Color: Greyed-Purple Group 185D.

*Seed formation.*—Not observed.

PLANT

Plant growth: Moderate upright to bushy. Very compact. When grown as an 8–11 cm pot plant on its own roots, the average height of the plant itself is 16 to 20 cm and the average width is 15 to 17 cm.

Stems:

*Color.*—Young wood: Yellow-Green Group 144A to 144B. Older wood: Yellow-Green Group 144A.

*Internodal distance.*—On mature canes, 18 to 20 mm.

*Length of stems.*—On average, canes are 10 to 13 cm from the base of the stem to the flowering portion.

*Diameter.*—3 mm.

*Surface texture.*—Young wood: Smooth. Older wood: Smooth.

Prickles:

*Incidence.*—5 prickles per 10 cm of stem.

*Length.*—4 mm.

*Shape.*—Upper side: Flat. Lower side: Flat.

*Color.*—Young wood: Greyed-Orange Group 173A. Mature wood: Greyed-Orange Group 160D to 173C.

Plant foliage: Normal number of leaflets on normal leaves in middle of the stem: 5 to 7 leaflets.

*Compound leaf size.*—65 mm to 70 mm (l)×45 to 55 mm (w).

*Quantity.*—4 to 5 leaves per 10 cm of stem.

*Color.*—Juvenile foliage: Upper Leaf Surface: Yellow-Green Group 146A to B. Anthocyanic intonations of Greyed-Yellow Group 160D to Greyed-Orange Group 173C on the upper margins and generalized throughout the leaflet. Lower Leaf Surface: Yellow-Green Group 146B. Mature foliage: Upper Leaf Surface: Yellow-Green Group 147A to 146A. Lower Leaf Surface: Yellow-Green Group 17B to 148B.

Plant leaves and leaflets:

*Stipules.*—Size: 6 to 9 mm in length. Shape: Linear, slightly broad based with outward extending apecies. Margins: Finely serrated with few stipitate glands. Color: Yellow-Green Group 146A to 147A.

*Petiole.*—Length: 12 mm on average. Diameter: Normally 1.5 mm. Upper surface: Color: Yellow-Green Group 146B with anthocyanic pigments of Greyed-Red Group 183C. Observations: Few stipitate glands. Lower surface: Color: Yellow-Green Group 146C. Observations: Few small prickles observed.

*Rachis.*—Size: Normally 22 mm. Upper surface: Color: Yellow-Green Group 146B with anthocyanic pigments of Greyed-Red Group 183C. Observations: Few stipitate glands. Lower surface: Color: Yellow-Green Group 146C. Observations: Few small prickles observed.

*Leaflet.*—Size: Normally 40 mm in length by 20 mm wide. Edge: Serrated. General Shape: Ovate. Apex Shape: Acute. Base Shape: Rounded. Texture: Smooth. Thickness: Average. Arrangement: Odd pinnate. Venation: Reticulate. Leaf Gloss: Moderate glossy finish.

Disease resistance: Average resistance to powdery and downy mildew, black spot, and *Botrytis* under normal glasshouse growing conditions in Denmark.

It is claimed:

1. A new and distinct variety of rose plant of the miniature class named 'Poulpar040', substantially as illustrated and described herein, due to its abundant, pink flowers, vigorous growth, compact habit, suitability for production from softwood cuttings in pots, and durable flowers and foliage that make the variety suitable for distribution in the floral industry.

* * * * *

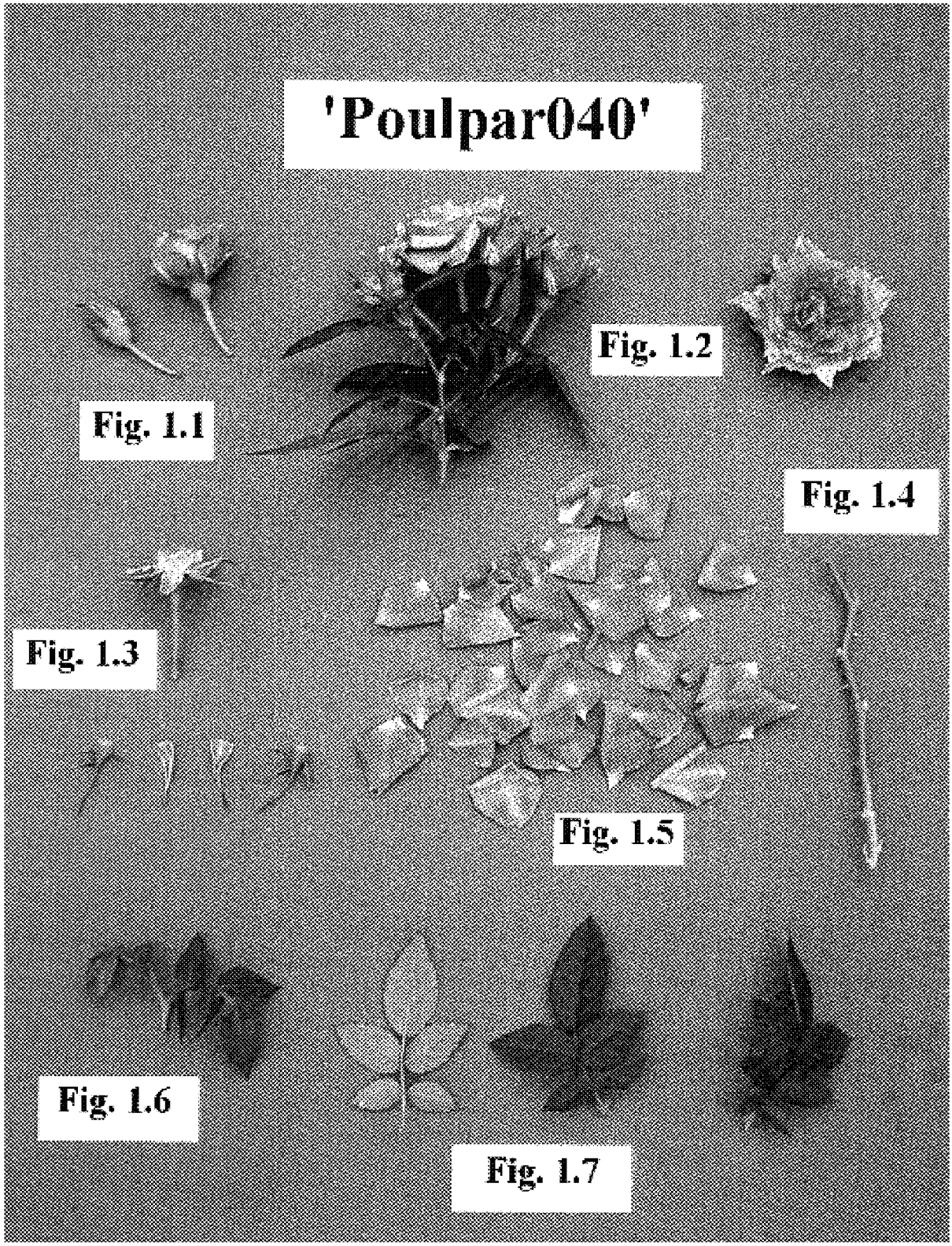
'Poulpar040'
Fig. 1.1
Fig. 1.2
Fig. 1.3
Fig. 1.4
Fig. 1.5
Fig. 1.6
Fig. 1.7